United States Patent [19]

Kurz et al.

[11] 4,424,147
[45] Jan. 3, 1984

[54] STABILIZATION OF PERCHLOROETHYLENE DIELECTRIC FLUIDS

[75] Inventors: Robert A. Kurz, Hermitage Township, Mercer County; Anthony J. Palumbo, Hermitage, both of Pa.

[73] Assignee: Westinghouse Electric Corp., Pittsburgh, Pa.

[21] Appl. No.: 413,592

[22] Filed: Aug. 31, 1982

[51] Int. Cl.³ .............................................. H01B 3/24
[52] U.S. Cl. ................................ 252/575; 174/17 LF; 174/23 C; 174/25 R; 174/25 C; 336/58; 336/94; 361/318; 570/111
[58] Field of Search ........................ 252/575; 570/111; 174/171 F, 23 C, 25 R, 25 C; 336/58, 94; 361/318

[56] References Cited

U.S. PATENT DOCUMENTS 2,722,561 11/1955 McCulloch .......................... 252/575
4,293,433 10/1981 Borror et al. ........................ 252/575
4,312,794 1/1982 Pearce et al. ........................ 252/578

Primary Examiner—John E. Kittle
Assistant Examiner—Robert A. Wax
Attorney, Agent, or Firm—R. D. Fuerle

[57] ABSTRACT

Disclosed is a method of inhibiting the attack by perchloroethylene on copper and organic polymers subject to said attack, such as parylene, by adding to perchloroethylene about 20 to about 1000 ppm of a stabilizer having the general formula

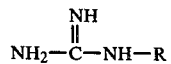

where

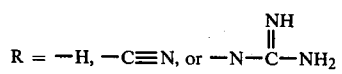

The preferred concentration of the stabilizer is about 40 to about 500 ppm. Also disclosed is an electrical apparatus containing copper or organic polymer subject to attack by perchloroethylene and perchloroethylene containing the stabilizer.

12 Claims, 1 Drawing Figure

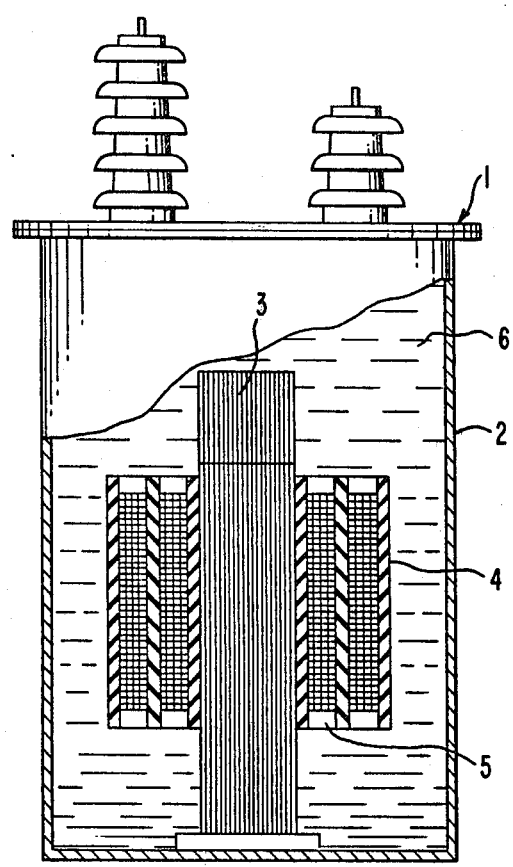

STABILIZATION OF PERCHLOROETHYLENE DIELECTRIC FLUIDS

CROSS-REFERENCE TO RELATED APPLICATION

This application is related to application Ser. No. 413,593, filed concurrently herewith by the same inventors, titled, "Perchloroethylene Stabilized with Aromatic Phenols."

BACKGROUND OF THE INVENTION

When polychlorinated biphenyls, used as a dielectric fluid in electrical equipment, were identified as an environmental hazard, a search was conducted for other fluids which could be used instead. One of the substitute fluids now being used is perchloroethylene, $C_2Cl_4$. In addition to being environmentally acceptable, perchloroethylene has a high dielectric strength and is nonflammable; it meets government and industry standards for use as a dielectric fluid in transformers.

When perchloroethylene is manufactured, various stabilizers are added to it such as N-methyl pyrrole and p-tertiary amylphenol (see U.S. Pat. No. 4,293,433). These stabilizers are anti-oxidants which are added to prevent the decomposition of the fluid.

While commercial perchloroethylene has good physical and electrical properties, it has been found that it badly corrodes copper in spite of the presence of the stabilizers already in it. The addition of some other commonly used stabilizers to commercial perchloroethylene, such as triazoles, was found to insignificantly reduce the corrosion rate of copper. Still other common stabilizers such as hydroquinone, actually increased the corrosion rate.

In addition, conductors in transformers are often insulated with polymers such as parylene. These polymers typically appear as thin coatings on conductors, either as strap or strip, which are then wound into coils. Commercially inhibited perchloroethylene was found to degrade these polymers, which could lead to electrical breakdown and failure of the transformer. Again, the addition of common stabilizers such as melamine to the commercial fluid did not prevent the degradation of the coatings.

SUMMARY OF THE INVENTION

We have found that dicyandiamide and a few related compounds substantially reduce the attack by perchloroethylene on copper and polymers such as parylene. While copper turns black from corrosion in the presence of commercially inhibited perchloroethylene, it remains a shiny copper color when dicyandiamide is added. Also, the degradation of polymers such as parylene is significantly lowered when dicyandiamide is added to commercially inhibited perchloroethylene, as indicated by a greatly reduced fall-off in dielectrical strength.

In addition, the dicyandiamide stabilizes the perchloroethylene itself. While the commercial fluid oxidizes to form suspended carbon particles, some of which settles on the transformer tank, this does not occur when dicyandiamide is added to the fluid. As these particles are electrically conductive, they are highly undesirable in a dielectric fluid.

DESCRIPTION OF THE DRAWING

The accompanying drawing is a side view in section of a certain presently preferred embodiment of a transformer containing a dielectric fluid stabilized according to this invention.

In the drawing, a transformer 1 is shown as comprising a sealed tank 2, a ferrous metal core 3 consisting of alternating layers of a conductor and an insulator, a primary coil 4, a secondary coil 5, and a dielectric fluid 6 which surrounds and convers the core and coils.

The stabilizers that are the subject of this invention have the general forumula

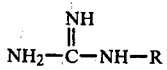

where

These compounds include

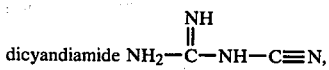

Of these compounds, dicyandiamide is preferred. About 20 to about 1000 parts per million (ppm) (based on the total weight of the dielectric fluid) of the stabilizer is used. Less than 20 ppm is ineffective and more than 1000 ppm is unnecessary. The preferred amount of stabilizer is about 40 to about 500 ppm. At room temperature, 40 ppm is the solubility limit of dicyandiamide, but it is preferable to use excess dicyandiamide to replace dicyandiamide which is used up, and to provide a source of dicyandiamide at higher temperatures where the solubility limit is higher.

The stabilizer may be used in combination with perchloroethylene alone or with a mixture of perchloroethylene and another dielectric fluid. For example, perchloroethylene is often used in combination with about 5 to about 30% mineral oil. The fluid may be used in all sorts of electrical apparatus including transformers, capacitors, cables, and circuit breakers. Much of this apparatus will contain metallic copper or organic polymers which are corroded by perchloroethylene such as parylene. Parylene is poly (para-xylene), and comes in two forms, parylene "C"

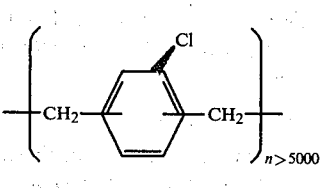

and parylene "N"

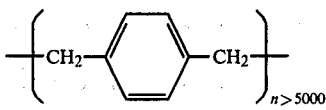

Parylene "C" is preferred as its properties are superior.

The following examples further illustrate this invention.

EXAMPLE 1

One gram of a copper braid 1¼ inch long by ¼ inch wide by 1/16 inch deep, made of finely woven wires was placed in sealed containers with various stabilizers and 2400 grams of perchloroethylene purchased from the Diamond Shamrock Company, which was analyzed as containing 55±5 ppm N - methylpyrrole. The containers were heated to 125° centigrade for various periods of time and the change in weight of the copper braid was measured. The following tables give us the results.

| STABILIZER ADDED | 30 days | 44 days | 90 days |
|---|---|---|---|
| None | | +5.14% | 12.96% |
| 0.05% benzotriazole | | +0.57% | +26.4% |
| 0.05% tolyltriazole | +5.7% | | |
| 0.05% hydroquinone | | +44% | |
| 0.05% dicyandiamide | | | −0.45% |

The above table shows that benzotriazole was ineffective in reducing corrosion after 44 days, and after 90 days it actually increased the amount of corrosion. Both tolyltriazole and hydroquinone also increased the rate of corrosion. Dicyandiamide, however, significantly and substantially reduced the corrosion of the copper.

EXAMPLE 2

Aluminum strips 2 inches wide and 5 mils thick coated with 0.8 mils of parylene "C" having a dielectric strength of 3546 volts/mil was placed in sealed containers containing the Diamond Shamrock perchloroethylene as described in Example 1 and various additional stabilizers. The containers were sealed and were aged at 125° C. for various periods of time after which the dielectric strength of the parylene film was again determined, if possible. The following table gives the results:

| | Dielectric Strength - % Retained | |
|---|---|---|
| STABILIZER ADDED | 120 days | 150 days |
| None | 62 | * |
| 0.05% dicyandiamide | 65 | 46 |
| 270 ppm dicyandiamide + paper (54 grams & 4400 grams C₂Cl₄) | 80 | 75 |

*untestable - film destroyed

The above results show that the presence of dicyandiamide in the perchloroethylene fluid greatly reduced its attack on parylene film.

EXAMPLE 3

Various stabilizers were added to the Diamond Shamrock perchloroethylene fluid described in Example 1 which were then stored for seven days at 125° C. in sealed stainless steel evacuated tanks. The following table gives the results:

| STABILIZER | RESULTS |
|---|---|
| None | Black particles of carbon suspended in fluid and settled out on tank |
| 0.05% dicyandiamide | Fluid clear, no black particles on tank |
| 0.05% melamine | No improvement |
| 0.05% hydroquinone paper (in ratio of 54 grams to 4400 grams C₂Cl₄) | Some improvement No improvement |

EXAMPLE 4

Two glass tubes were half filled with 50 cc of a mixture of 75% of the Diamond Shamrock perchloroethylene described in Example 1 and 25% mineral oil, and to one of the tubes was added 0.05% dicyandiamide. The tubes were evacuated, sealed, and aged for 80 days at 125° C. After aging, the dissipation factor of the first tube was 19.5%, but the dissipation factor of the tube containing dicyandiamide was only 0.75%.

What is claimed is:

1. A method of protecting copper and synthetic organic polymers from attack by perchloroethylene comprising adding to said perchloroethylene about 20 to about 1000 ppm of a compound having a general formula

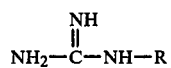

where R is

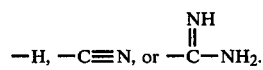

2. A method according to claim 1 wherein said organic polymer is parylene.

3. A method according to claim 1 wherein

R is—C≡N.

4. A method according to claim 1 wherein said perchloroethylene is a dielectric fluid in a transformer.

5. A method according to claim 1 wherein said perchloroethylene is mixed with about 5 to about 30% mineral oil.

6. A method according to claim 1 wherein the amount of said compound is about 40 to about 500 ppm.

7. In an electrical apparatus containing perchloroethylene dielectric fluid in contact with copper or a synthetic organic polymer which is vulnerable to attack by said perchloroethylene, the improvement which comprises including in said fluid about 20 to about 1000 ppm of a compound having a general formula

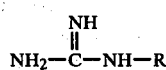

where $$R = -H, -C\equiv N, \text{ or } -\overset{\overset{NH_2}{\|}}{C}-NH_2.$$

8. Electrical apparatus according to claim 7 wherein the amount of said compound is about 40 to about 500 ppm.

9. Electrical apparatus according to claim 7 wherein R is —C≡N.

10. Electrical apparatus according to claim 7 wherein said electrical apparatus is a transformer.

11. Electrical apparatus according to claim 7 wherein said organic polymer is parylene.

12. Electrical apparatus according to claim 7 wherein said perchloroethylene is mixed with about 5 to 30% mineral oil.

* * * * *